United States Patent [19]

Lesher et al.

[11] 4,294,836

[45] Oct. 13, 1981

[54] 1,3-DIHYDRO-6-(PYRIDINYL)-2H-IMIDAZO[4,5-b]PYRIDIN-2-ONES AND -IMIDAZO[4,5-b]PYRIDINE-2-THIONES AND THEIR CARDIOTONIC USE

[75] Inventors: George Y. Lesher, Schodack; Ruth P. Brundage, East Greenbush, both of N.Y.

[73] Assignee: Sterling Drug Inc., New York, N.Y.

[21] Appl. No.: 132,907

[22] Filed: Mar. 24, 1980

[51] Int. Cl.³ .................. C07D 471/04; A61K 31/415
[52] U.S. Cl. .............................. 424/263; 424/248.51; 424/248.57; 544/127; 546/118
[58] Field of Search .................. 546/118; 544/127; 424/248.51, 248.57, 263

[56] References Cited

U.S. PATENT DOCUMENTS

| | | | |
|---|---|---|---|
| 3,838,156 | 9/1974 | Brundage et al. | 260/295.5 R |
| 4,072,746 | 2/1978 | Lesher et al. | 424/263 |
| 4,152,434 | 5/1979 | Schwiesguth | 544/127 |
| 4,195,088 | 3/1980 | Barzaghi et al. | 546/118 |

FOREIGN PATENT DOCUMENTS 1322318  7/1973  United Kingdom .

OTHER PUBLICATIONS

Baldwin et al., *Jour. of Medicinal Chemistry,* vol. 20, pp. 1189–1193 (1977).

*Primary Examiner*—John M. Ford
*Attorney, Agent, or Firm*—Robert K. Bair; B. Woodrow Wyatt

[57] ABSTRACT

1,3-Dihydro-3-R-5-PY-2H-imidazo[4,5-b]pyridin-2-ones or 2-thiones or pharmaceutically-acceptable acid-addition salts thereof, which are useful as cardiotonic agents, where R is hydrogen, lower-alkyl, lower-hydroxyalkyl, 2,3-dihydroxypropyl, lower-alkoxyalkyl or Y-NB where Y is lower-alkylene and NB is di-(lower-alkyl)amino or 4-morpholinyl, and PY is 4- or 3-pyridinyl or 4- or 3-pyridinyl having one or two lower-alkyl substituents, are prepared by reacting a 3-amino-2-RNH-6-PY-pyridine with urea or carbonyldiimidazole to produce said -2-ones or with an alkali metal xanthate, thiourea or thiocarbonyldiimidazole to produce said -2-thiones. Also shown is the preparation of the intermediate 3-amino-2-RNH-6-PY-pyridines.

14 Claims, No Drawings

1,3-DIHYDRO-6-(PYRIDINYL)-2H-IMIDAZO[4,5-b]PYRIDIN-2-ONES AND-IMIDAZO[4,5-b]-PYRIDINE-2-THIONES AND THEIR CARDIOTONIC USE

BACKGROUND OF THE INVENTION (a) Field of the Invention

This invention relates to 2H-imidazo[4,5-b]-pyridin-2-ones or -2-thiones, their preparation and their use as cardiotonics.

(b) Description of the Prior Art

Baldwin et al. [J. Med. Chem. 20, 1189–1193 (1977)] prepared 2-(3-pyridinyl)-1H-imidazo[4,5-b]pyridine and 2-(4-pyridinyl)-1H-imidazo[4,5-b]pyridine by heating, respectively, a mixture of 2,3-diaminopyridine and nicotinic acid or a mixture of 2,3-diminopyridine and isonicotinic acid. Both of these compounds were found by Baldwin et al. to be inactive when tested as inhibitors of xanthine oxidase.

Lesher and Gruett British Pat. No. 1,322,318, published July 4, 1973, shows as intermediates for preparing antibacterially-active 1-alkyl-1,4-dihydro-4-oxo-7-PY-1,8-naphthyridine-3-carboxylic acids and esters (where PY is 4- or 3-pyridinyl or 4- or 3-pyridinyl having one or two lower-alkyl substituents) the following illustrative reaction sequence (Examples 1C through 1G and 2C through 2G): the preparation of 1,2-dihydro-2-oxo-6-(4- or 3-pyridinyl)nicotinonitrile, its hydrolysis and decarboxylation to produce 6-(4- or 3-pyridinyl)-2(1H)-pyridinone, its chlorination with phosphorus oxychloride to produce 2-chloro-6-(4- or 3-pyridinyl)pyridine, its reaction with hydrazine to produce 2-hydrazino-6-(4- or 3-pyridinyl)pyridine and its catalytic hydrogenation using Raney nickel to produce 2-amino-6-(4- or 3-pyridinyl)pyridine also useful as an intermediate to produce said antibacterially-active 1,8-naphthyridines.

Brundage and Lesher U.S. Patent 3,838,156, issued Sept. 24, 1974, discloses as sequential intermediates 1,2-dihydro-2-oxo-6-Q'''-nicotinic acids, 2-halo-6-Q'''-nicotinic acids and 2-RNH-6-Q'''-nicotinic acids, where Q''' is 4(or 3)-pyridinyl or 4(or 3)-pyridinyl having one or two lower-alkyl substituents, halo is chloro or bromo, and R is lower-alkyl.

Lesher and Opalka U.S. Pat. No. 4,072,746, issued Feb. 7, 1978, discloses the following reaction sequences: (a) hydrolysis of 1,2-dihydro-2-oxo-5-PY-nicotinonitrile to produce 1,2-dihydro-2-oxo-5-PY-nicotinic acid, decarboxylation of said nicotinic acid to produce 5-PY-2(1H)-pyridinone, nitration of either said nicotinic acid or said 2(1H)-pyridinone to produce 3-nitro-5-PY-2(1H)-pyridinone and reduction of the 3-nitro compound to produce 3-amino-5-PY-2(1H)-pyridinone; and, (b) the reaction of 5-PY-2(1H)-pyridinone with halogen, preferably bromine or chlorine, to produce 3-halo-5-PY-2(1H)-pyridinone and reacting said halo compound with $R_1R_2NH$ to produce 3-$R_1R_2N$-5-PY-2(1H)-pyridinone. In the above two reaction sequences $R_1$ is lower-alkyl, $R_2$ is hydrogen or lower-alkyl and PY is 4- or 3- or 2-pyridinyl or 4- or 3- or 3-pyridinyl having one or two lower-alkyl substituents. Of the various compounds in said two sequences, the 3-amino-5-PY-2(1H)-pyridinones, 3-$R_1R_2N$-5-PY-2(1H)-pyridinones, the 1,2-dihydro-2-oxo-5-PY-2(1H)-nicotinonitriles and the 5-PY-2(1H)-pyridinones had cardiotonic activity; all others were intermediates as were the 1,2-dihydro-2-oxo-5-PY-2(1H)-nicotinonitriles and 5-PY-2(1H)-pyridinones.

SUMMARY OF THE INVENTION

In a composition of matter aspect, the invention relates to 1,3-dihydro-3-R-5-PY-2H-imidazo[4,5-b]pyridin-2-ones or -2-thiones or pharmaceutically-acceptable acid-addition salts thereof, which are useful as cardiotonic agents where R and PY have the meanings given hereinbelow.

The invention in a process aspect comprises reacting a 3-amino-2-RNH-6-PY-pyridine with urea or carbonyldiimidazole to produce 1,3-dihydro-3-R-5-PY-2H-imidazo[4,5-b]pyridin-2-one or with an alkali metal lower-alkyl xanthate, thiourea or thiocarbonyldiimidazole to produce 1,3-dihydro-3-R-5-PY-2H-imidazo-[4,5-b]pyridine-2-thione. This process aspect is disclosed and claimed in copending divisional application Ser. No. 237,732, filed Feb. 20, 1981.

A composition aspect of the invention relates to a cardiotonic composition for increasing cardiac contractility in a patient, said composition comprising a pharmaceutically-acceptable carrier and, as the active ingredient thereof, an effective amount of a cardiotonic 1,3-dihydro-3-R-5-PY-2H-imidazo[4,5-b]pyridin-2-one or -2-thione or pharmaceutically-acceptable acid-addition salt thereof.

In a method aspect, the invention relates to a method for increasing cardiac contractility in a patient requiring such treatment which comprises the administration of a medicament comprising a pharmaceutically-acceptable carrier and, as the active component, thereof, an effective amount of the cardiotonic 1,3-dihydro-1-3-R-5-PY-2H-imidazo[4,5-b]pyridin-2-one or 2-thione or pharmaceutically-acceptable acid-addition salt thereof.

Another composition of matter aspect relates to a 3-amino-2-RNH-6-PY-pyridine or pharmaceutically-acceptable acid-addition salt thereof, which is useful as an intermediate as shown above.

Another process aspect of the invention comprises the steps of reacting 2-halo-3-nitro-6-PY-pyridine with ammonia or an amine of the formula $RNH_2$, where halo, PY and R are defined hereinbelow, to produce 2-RNH-3-nitro-6-PY-pyridine and reducing the latter compound to produce 3-amino-2-RNH-6-PY-pyridine. This process aspect is disclosed and claimed in copending divisional application Ser. No. 237,732, filed Feb. 20, 1981.

DETAILED DESCRIPTION INCLUSIVE OF PREFERRED EMBODIMENTS

In a composition of matter aspect the invention resides in a 1,3-dihydro-3-R-5-PY-2H-imidazo[4,5-b]pyridin-2-one or 2-thione having the formula I

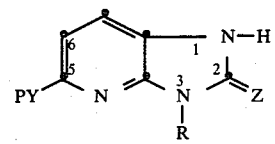

where Z is O or S, R is hydrogen, lower-alkyl, lower-hydroxyalkyl, 2,3-dihydroxypropyl, lower-alkoxyalkyl or Y-NB where Y is lower-alkylene having at least two carbon atoms between its connecting linkages and NB is di-(lower-alkyl)amino or 4-morpholinyl, and PY is 4- or 3-pyridinyl or 4- or 3-pyridinyl having one or two lower-alkyl substituents, or pharmaceutically-acceptable acid-addition salts thereof. The compounds of formula I are useful as cardiotonic agents, as determined by standard pharmacological evaluation procedures. Preferred embodiments are those of formula I where PY is 4-pyridinyl or 3-pyridinyl, Z is O or S, R is hydrogen, methyl, ethyl or 2-hydroxyethyl.

The compound of formula I may exist in tautomeric forms, that is, as 1,3-dihydro-3-R-5-PY-2H-imidazo[4,5-b]-pyridin-2-one or -2-thione of formula I and/or 3-R-5-PY-3H-imidazo[4,5-b]pyridin-2-ol or -2-thiol of formula I A, illustrated as follows

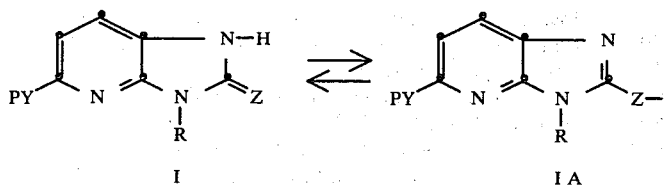

Structural preferences for other known imidazo[4,5-b]pyridin-2-ones or -2-thiones would indicate the above formula I to be the preferred tautomeric structure; thus, it is preferred to use the names based on structure I, although it is understood that either or both structures are comprehended herein. When R is hydrogen, a third tautomeric form may exist, that is, 5-PY-1H-imidazo[4,5-b]pyridin-2-ol or -2-thiol (IB), and is also comprehended herein.

In a process aspect the invention resides in the process of producing the 1,3-dihydro-3-R-5-PY-2H-imidazo-[4,5-b]pyridin-2-one or -2-thione of formula I which comprises reacting 3-amino-2-RNH-6-PY-pyridine (II) with urea or carbonyldiimidazole to produce 1,3-dihydro-3-R-6-PY-2H-imidazo[4,5-b]-pyridin-2-one (I where Z is O) or with an alkali metal xanthate, thiourea or thiocarbonyldiimidazole to produce 1,3-dihydro-3-R-6-PY-2H-imidazo[4,5-b]pyridine-2-thione (I where Z is S), where PY, R and Z have the meanings given above for the compound of formula I. Preferred embodiments of this process are those which produce the above-said preferred composition embodiments of formula I.

A composition aspect of the invention resides in a cardiotonic composition for increasing cardiac contractility, said composition comprising a pharmaceutically-acceptable carrier and, as the active component thereof, an effective amount of a cardiotonic 1,3-dihydro-3-R-5-PY-2H-imidazo[4,5-b]pyridin-2-one (I where Z is O) or -2-thione (I where Z is S) of formula I, where Z, R and PY are each defined as in formula I, or pharmaceutically-acceptable acid-addition salt thereof. Preferred embodiments are those having as active components the above-said preferred embodiments of formula I.

A method aspect of the invention resides in the method for increasing cardiac contractility in a patient requiring such treatment which comprises administering orally or parenterally in a solid or liquid dosage form to said patient an effective amount of a cardiotonic 1,3-dihydro-3-R-5-PY-2H-imidazo[4,5-b]pyridin-2-one (I where Z is O) or -2-thione (I where Z is S) of formula I where PY, R and Z are defined as in formula I, or pharmaceutically-acceptable acid-addition salts thereof. Preferred embodiments of this method aspect are those using the preferred cardiotonics of formula I noted above.

In another composition of matter aspect, the invention resides in the 3-amino-2-RNH-6-PY-pyridine (II) or pharmaceutically-acceptable acid-addition salt thereof, where R is hydrogen, lower-alkyl, lower-hydroxyalkyl, 2,3-dihydroxypropyl, lower-alkoxyalkyl or Y-NB where Y is lower-alkylene having at least two carbon atoms between its connecting linkages and NB is di-(lower-alkyl)amino or 4-morpholinyl, and PY is 4- or 3-pyridinyl or 4- or 3-pyridinyl having one or two lower-alkyl substituents. These compounds (II) are useful as intermediates in the preparation of the compounds having formula I. Preferred embodiments are those where PY is 4-pyridinyl or 3-pyridinyl, and R is hydrogen, methyl, ethyl or 2-hydroxyethyl.

In another process aspect, the invention resides in the process which comprises the steps of reacting 2-halo-3-nitro-6-PY-pyridine (III) with ammonia or an amine of the formula RNH₂ to produce 2-RNH-3-nitro-6-PY-pyridine (IV) and reducing the 3-nitro compound (IV) to produce 3-amino-2-RNH-6-PY-pyridine (II) where halo is chloro or bromo, and R and PY are defined as hereinabove for the compounds of formula I. Preferred embodiments of this process are those where halo is chloro and which produce the above-said preferred embodiments of 3-amino-2-RNH-6-PY-pyridine (II).

The term "lower-alkyl" as used herein, e.g., as one of the meanings for R or as a substituent for PY in formula I, means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of PY in formula I where PY is 4-, 3- or 2-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-hydroxyalkyl" as used herein, e.g., for one of the meanings for R in formula I, means hydroxyalkyl radicals having from two to six carbon atoms which can be arranged as straight or branched chains and at least two carbon atoms of which separate hydroxy and the 1-ring or 3-ring nitrogen atom of the imidazo[4,5-b]pyridine ring, illustrated by 2-hydroxyethyl, 3-hydroxypropyl, 2-hydroxypropyl, 4-hydroxybutyl, 3-hydroxybutyl, 5-hydroxyamyl, 6-hydroxyhexyl, and the like.

The term "lower-alkoxyalkyl" as used herein, e.g., for one of the meanings for R in formula I, means alkoxyalkyl radicals having from three to six carbon atoms which can be arranged as straight or branched chains and at least two carbon atoms of which separate the oxygen atom of alkoxyalkyl and the 1-ring or 3-ring nitrogen atom of the imidazo[4,5-b]pyridine ring, illustrated by 2-methoxyethyl, 2-ethoxyethyl, 3-methoxypropyl, 2-methoxypropyl, 2-methoxybutyl, 4-ethoxybutyl, 3-ethoxypropyl, 3-n-propoxypropyl, and the like.

The term "lower-alkylene" designated as Y as part of R herein means lower-alkylene radicals having at least two carbon atoms between its connecting linkages and having from two to six carbon atoms which can be arranged as branched or straight chains, illustrated by —CH$_2$CH$_2$—,

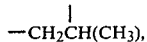

—CH(CH$_3$)CH$_2$—,

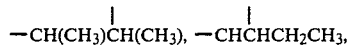

—(CH$_2$)$_3$—, —(CH$_2$)$_4$—, —(CH$_2$)$_5$—, —(CH$_2$)$_6$—,

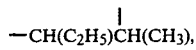

and the like.

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form or the hydrochloride salt; however, appropriate pharmaceutically-acceptable salts within the scope of the invention are those derived from other mineral acids such as hydrobromic acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, lactate, tartrate, methanesulfonate, ethanesulfonate, benzenesulfonate, cyclohexylsulfamate and quinate, respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I) are preferred, all acid-addition salts are within the scope of our invention. All acid-addition salts are useful as sources of the free base form even if the particular salt per se is desired only as an intermediate product, as for example when the salt is formed only for purposes of purification or identification, or when it is used as an intermediate in preparing a pharmaceutically-acceptable salt by ion exchange procedures.

The molecular structure of the compound of formula I was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same, as follows.

The preparation of 1,3-dihydro-3-R-2H-imidazo-[4,5-b]pyridin-2-one (I, Z is O) by reacting 3-amino-2-RNH-6-PY-pyridine (II) with urea is conveniently and preferably carried out by heating the reactants in refluxing dimethylformamide. Alternatively, other suitable solvents can be used, e.g., dioxane, nitrobenzene, etc. This preparation can be run using carbonyldiimidazole in place of urea preferably by mixing the reactants in dimethylformamide at about 25°–50° C. for about one to three hours and then, if needed, heating the reaction mixture at about 70°–80° C. for about two to sixteen hours; alternatively, other solvents, e.g., dioxane, etc. can be used here.

The preparation of 1,3-dihydro-3-R-2H-imidazo[4,5-b]-pyridine-2-thione (I, Z is S) by reacting 3-amino-2-RNH-6-PY-pyridine (II) with an alkali metal xanthate or thiourea is carried out by heating the reactants in a suitable solvent at about 60° C. to 100° C., preferably about 75° C. to 85° C. The reaction using an alkali metal xanthate, preferably the sodium or potassium salt, is conveniently run by refluxing the reactants in a mixture of water and a lower-alkanol, preferably aqueous ethanol. The reaction using thiourea is conveniently run by heating the reactants in refluxing dimethylformamide. The reaction using thiocarbonyldiimidazole is conveniently run at room temperature or up to about 40°–60° C. in dimethylformamide.

The reaction of the 2-halo-3-nitro-6-PY-pyridine (III) with ammonia or an amine of the formula RNH$_2$ to obtain 2-RNH-3-nitro-6-PY-pyridine (IV) is run by heating the reactants, preferably under pressure using ammonia or source thereof and monomethylamine and at atmospheric pressure using other higher primary amines.

The reaction of 2-RNH-3-nitro-6-PY-pyridine (IV) to obtain 3-amino-2-RNH-6-PY-pyridine is preferably carried out by catalytic hydrogenation of IV using a suitable catalyst, e.g., 10% palladium-on-charcoal, Raney nickel, and the like, in a suitable solvent. A preferred solvent was the combination of dimethylformamide and ethanol.

The preparation of the intermediate 2-halo-3-nitro-6-PY-pyridine (III) is conveniently carried out in two steps by first nitrating the known 6-PY-2(1H)-pyridine (V) to produce 3-nitro-6-PY-2(1H)-pyridinone (VI) and then reacting VI with an inorganic halogenating agent, preferably by refluxing the 2(1H)-pyridinone (VI) with phosphorus oxychloride in dimethylformamide. This two step preparation of III is further illustrated hereinbelow in Examples A-1 through A-8 and B-1 through B-9.

The following examples will further illustrate the invention without, however, limiting it thereto.

A. 3-NITRO-6-PY-2(1H)-PYRIDINONES

A-1. 3-Nitro-6-(4-pyridinyl)-2(1H)-pyridinone—To a solution warmed to 78° C. and containing 413 g. of 6-(4-pyridinyl)-2(1H)-pyridinone in 1600 ml. of concentrated sulfuric acid was added dropwise with stirring over a period of about three hours a mixture containing 320 ml. of 90% nitric acid and 160 ml. of concentrated sulfuric acid; the addition of sulfuric acid was at such a rate as to keep the reaction temperature at about 75°–90° C. One hour after the sulfuric acid addition had been completed, the reaction temperature had dropped to 40° C. and stirring was continued at this temperature for one hour. The reaction mixture was then poured into ice. To the mixture was added concentrated ammonium hydroxide to a pH of about 6, together with more ice. The mixture was then cooled in a refrigerator and allowed to stand overnight. The separated solid was collected, washed successively with water, a little ethanol and ether, and then dried in vacuo at 55° C. overnight to yield 277 g. of 3-nitro-4-(pyridinyl)-2(1H)-pyridinone, m.p. >300° C.

Following the procedure described in Example A-1 but using in place of 6-(4-pyridinyl)-2(1H)-pyridinone a molar equivalent quantity of the appropriate 6-PY-2(1H)-pyridinone, it is contemplated that the corresponding 3-nitro-6-PY-2(1H)-pyridinones of Examples A-2 through A-8 can be obtained.

A-2. 3-Nitro-6-(3-pyridinyl)-2(1H)-pyridinone.
A-3. 6-(2-Methyl-4-pyridinyl)-3-nitro-2(1H)-pyridinone.
A-4. 6-(3-Methyl-4-pyridinyl)-3-nitro-2(1H)-pyridinone.
A-5. 6-(2-Ethyl-4-pyridinyl)-3-nitro-2(1H)-pyridinone.
A-6. 6-(3-Ethyl-4-pyridinyl)-3-nitro-2(1H)-pyridinone.
A-7. 6-(2,6-Dimethyl-4-pyridinyl)-3-nitro-2(1H)-pyridinone.
A-8. 6-(3,5-Dimethyl-4-pyridinyl)-3-nitro-2(1H)-pyridinone.

B. 2-HALO-3-NITRO-6-PY-PYRIDINES

B-1. 2-Chloro-3-nitro-6-(4-pyridinyl)pyridine—A mixture containing 277 g. of 3-nitro-6-(4-pyridinyl)-2(1H)-pyridinone, 4400 ml. of dimethylformamide and 470 ml. of phosphorus oxychloride was heated with stirring on a steam bath for about forty minutes, during which time dissolution resulted. The reaction mixture was allowed to cool and then was poured into 15 liters of a mixture of ice and water. The resulting clear solution was neutralized with concentrated ammonium hydroxide. The solid that precipitated was collected, washed with water, air-dried, and then triturated with six three-liter portions of boiling cyclohexane, recycling the solvent after collected by filtration the yellow crystalline product from each cooled extract. There was thus obtained 120 g. of 2-chloro-3-nitro-6-(4-pyridinyl)-pyridine, m.p. 107°–110° C.

Following the procedure of Example B-1 but using in place of phosphorus oxychloride a molar equivalent quantity of phosphorus oxybromide or phosphorus tribromide, it is contemplated that the corresponding 2-bromo compound of Example B-2 can be obtained.

B-2. 2-Bromo-3-nitro-6-(4-pyridinyl)pyridine.

Following the procedure described in Example B-1 but using in place of 3-nitro-6-(4-pyridinyl)-2(1H)-pyridinone a molar equivalent quantity of the appropriate 3-nitro-6-PY-2(1H)-pyridinone, it is contemplated that there can be obtained the corresponding 2-chloro-3-nitro-6-PY-pyridines of Examples B-3 through B-9.

B-3. 2-Chloro-3-nitro-6-(3-pyridinyl)pyridine.
B-4. 2-Chloro-6-(2-methyl-4-pyridinyl)-3-nitropyridine.
B-5. 2-Chloro-6-(3-methyl-4-pyridinyl)-3-nitropyridine.
B-6. 2-Chloro-6-(2-ethyl-4-pyridinyl)-3-nitropyridine.
B-7. 2-Chloro-6-(3-ethyl-4-pyridinyl)-3-nitropyridine.
B-8. 2-Chloro-6-(2,6-dimethyl-4-pyridinyl)-3-nitropyridine.
B-9. 2-Chloro-6-(3,5-dimethyl-4-pyridinyl)-3-nitropyridine.

C. 2-RNH-3-NO$_2$-6-PY-PYRIDINES

C-1. 2-Amino-3-nitro-6-(4-pyridinyl)pyridine—A mixture containing 120 g. of 2-chloro-3-nitro-6-(4-pyridinyl)pyridine, 900 ml. of 95% ethanol and 510 ml. of concentrated ammonium hydroxide was autoclaved at 60° C. for twenty hours. The reaction mixture was cooled and the separated solid was collected, washed successively with ethanol and ether, and dried to yield 102 g. of 2-amino-3-nitro-6-(4-pyridinyl)pyridine, m.p. 216°–218° C.

Following the procedure described in Example C-1 but using in place of 2-chloro-3-nitro-6-(4-pyridinyl)-pyridine a molar equivalent quantity of 2-chloro-3-nitro-6-PY-pyridine, it is contemplated that there can be obtained the corresponding 2-amino-3-nitro-6-PY-pyridines of Examples C-2 through C-8.

C-2. 2-Amino-3-nitro-6-(3-pyridinyl)pyridine.
C-3. 2-Amino-6-(2-methyl-4-pyridinyl)-3-nitropyridine.
C-4. 2-Amino-6-(3-methyl-4-pyridinyl)-3-nitropyridine.
C-5. 2-Amino-6-(2-ethyl-4-pyridinyl)-3-nitropyridine.
C-6. 2-Amino-6-(3-ethyl-4-pyridinyl)-3-nitropyridine.
C-7. 2-Amino-6-(2,6-dimethyl-4-pyridinyl)-3-nitropyridine.
C-8. 2-Amino-6-(3,5-dimethyl-4-pyridinyl)-3-nitropyridine.

Following the procedure described in Example C-1 but using in place of ammonia a molar equivalent quantity of the appropriate amine of the formula RNH$_2$, it is contemplated that there can be obtained the corresponding 2-RNH-3-nitro-6-(4-pyridinyl)pyridines of Examples C-9 through C-18.

C-9. 2-Methylamino-3-nitro-6-(4-pyridinyl)pyridine.
C-10. 2-Ethylamino-3-nitro-6-(4-pyridinyl)pyridine.
C-11. 2-Isopropylamino-3-nitro-6-(4-pyridinyl)pyridine.
C-12. 2-n-Butylamino-3-nitro-6-(4-pyridinyl)pyridine.
C-13. 2-n-Hexylamino-3-nitro-6-(4-pyridinyl)pyridine.
C-14. 2-(2-Hydroxyethylamino)-3-nitro-6-(4-pyridinyl)-pyridine.
C-15. 2-(2,3-Dihydroxypropylamino)-3-nitro-6-(4-pyridinyl)pyridine.
C-16. 2-(2-Dimethylethylamino)-3-nitro-6-(4-pyridinyl)-pyridine.
C-17. 2-(2-Methoxyethylamino)-3-nitro-6-(4-pyridinyl)-pyridine.
C-18. 2-[2-(4-Morpholinyl)ethylamino]-3-nitro-6-(4-pyridinyl)pyridine.

D. 3-AMINO-2-RNH-6-PY-PYRIDINES

D-1. 2,3-Diamino-6-(4-pyridinyl)pyridine—A mixture containing 43.2 g. of 2-amino-3-nitro-6-(4-pyridinyl)pyridine, 360 ml. of dimethylformamide, 220 ml. of ethanol and 1 g. of 10% palladium-on-charcoal was shaken in a Parr apparatus under catalytic hydrogenation conditions for about one hour. The reaction mixture was filtered and the filtrate concentrated in vacuo to a volume of about 150 ml. and cooled. The separated solid was collected and dried to produce 20 g. of 2,3-diamino-6-(4-pyridinyl)pyridine which can be used directly in the next step without further purification. In another run, a sample was recrystallized from ethanol using decolorizing charcoal to produce the product, 2,3-diamino-6-(4-pyridinyl)-pyridine, melting at 252°–254° C.

Following the procedure described in Example D-1 using in place of 2-amino-3-nitro-6-(4-pyridinyl)pyridine a molar equivalent quantity of the appropriate 2-amino-3-nitro-6-PY-pyridine, it is contemplated that there can be obtained the corresponding 2,3-diamino-6-PY-pyridines of Examples D-2 through D-8.

D-2. 2,3-Diamino-6-(3-pyridinyl)pyridine.
D-3. 2,3-Diamino-6-(2-methyl-4-pyridinyl)pyridine.
D-4. 2,3-Diamino-6-(3-methyl-4-pyridinyl)pyridine.
D-5. 2,3-Diamino-6-(2-ethyl-4-pyridinyl)pyridine.
D-6. 2,3-Diamino-6-(3-ethyl-4-pyridinyl)pyridine.
D-7. 2,3-Diamino-6-(2,6-dimethyl-4-pyridinyl)pyridine.
D-8. 2,3-Diamino-6-(3,5-dimethyl-4-pyridinyl)pyridine.

Following the procedure described in Example D-1 but using in place of 2-amino-3-nitro-6-(4-pyridinyl)-pyridine a molar equivalent quantity of the appropriate 2-RNH-3-nitro-6-PY-pyridine, it is contemplated that there can be obtained the corresponding 3-amino-2-RNH-6-(4-pyridinyl)pyridines of Examples D-9 through D-18.

D-9. 3-Amino-2-methylamino-6-(4-pyridinyl)pyridine.
D-10. 3-Amino-2-ethylamino-6-(4-pyridinyl)pyridine.
D-11. 3-Amino-2-isopropylamino-6-(4-pyridinyl)pyridine.
D-12. 3-Amino-2-n-butylamino-6-(4-pyridinyl)pyridine.
D-13. 3-Amino-2-n-hexylamino-6-(4-pyridinyl)pyridine.
D-14. 3-Amino-2-(2-hydroxyethylamino)-6-(4-pyridinyl)-pyridine.
D-15. 3-Amino-2-(2,3-dihydroxypropylamino)-6-(4-pyridinyl)pyridine.
D-16. 3-Amino-2-(2-dimethylaminoethylamino)-6-(4-pyridinyl)pyridine.
D-17. 3-Amino-2-(2-methoxyethylamino)-6-(4-pyridinyl)-pyridine.
D-18. 3-Amino-2-[2-(4-morpholinyl)ethylamino]-6-(4-pyridinyl)pyridine.

E. 1,3-DIHYDRO-3-R-5-PY-2H-IMIDAZO[4,5-b]PYRIDIN-2-ONES

E-1. 1,3-Dihydro-5-(4-pyridinyl)-2H-imidazo[4,5-b]-pyridin-2-one—To a warm (45° C.) solution of 11.2 g. of 2,3-diamino-6-(4-pyridinyl)pyridine in 100 ml. of dimethylformamide was added with stirring 10.5 g. of 1,1'-dicarbonyldiimidazole. Solid began to separate within a few minutes. The reaction mixture was stirred with no external heating for about 40 minutes (temperature of 45° C. with no change in appearance after the first ten minutes) and then heated to 80° C. (no change in appearance). The separated solid was collected, washed and triturated with ethanol and dried at 70° C. in vacuo to yield 11.3 g. of 1,3-dihydro-5-(4-pyridinyl)-2H-imidazo[4,5-b]pyridin-2-one, m.p. >300° C.

Following the procedure described in Example E-1 but using in place of 2,3-diamino-6-(4-pyridinyl)pyridine a molar equivalent quantity of the appropriate 2,3-diamino-6-PY-pyridine, it is contemplated that there can be obtained the corresponding 1,3-dihydro-5-PY-2H-imidazo[4,5-b]pyridin-2-ones of Examples E-2 through E-8.

E-2. 1,3-Dihydro-5-(3-pyridinyl)-2H-imidazo[4,5-b]pyridin-2-one.
E-3. 1,3-Dihydro-5-(2-methyl-4-pyridinyl)-2H-imidazo[4,5-b]pyridin-2-one.
E-4. 1,3-Dihydro-5-(3-methyl-4-pyridinyl)-2H-imidazo[4,5-b]pyridin-2-one.
E-5. 1,3-Dihydro-5-(2-ethyl-4-pyridinyl)-2H-imidazo[4,5-b]pyridin-2-one.
E-6. 1,3-Dihydro-5-(3-ethyl-4-pyridinyl)-2H-imidazo[4,5-b]pyridin-2-one.
E-7. 1,3-Dihydro-5-(2,6-dimethyl-4-pyridinyl)-2H-imidazo[4,5-b]pyridin-2-one.
E-8. 1,3-Dihydro-5-(3,5-dimethyl-4-pyridinyl)-2H-imidazo[4,5-b]pyridin-2-one.

Following the procedure described in Example E-1 but using in place of 2,3-diamino-6-(4-pyridinyl)pyridine a molar equivalent quantity of the appropriate 2-RNH-3-amino-6-(4-pyridinyl)pyridine, it is contemplated that there can be obtained the corresponding 1,3-dihydro-3-R-5-(4-pyridinyl-2H-imidazo[4,5-b]pyridin-2-ones of Examples E-9 through E-18.

E-9. 1,3-Dihydro-3-methyl-5-(4-pyridinyl)-2H-imidazo[4,5-b]pyridin-2-one.
E-10. 3-Ethyl-1,3-dihydro-5-(4-pyridinyl)-2H-imidazo[4,5-b]pyridin-2-one.
E-11. 1,3-Dihydro-3-isopropyl-5-(4-pyridinyl)-2H-imidazo[4,5-b]pyridin-2-one.
E-12. 3-n-Butyl-1,3-dihydro-5-(4-pyridinyl)-2H-imidazo[4,5-b]pyridin-2-one.
E-13. 3-n-Hexyl-1,3-dihydro-5-(4-pyridinyl)-2H-imidazo[4,5-b]pyridin-2-one.
E-14. 1,3-Dihydro-3-(2-hydroxyethyl)-5-(4-pyridinyl)-2H-imidazo[4,5-b]pyridin-2-one.
E-15. 1,3-Dihydro-3-(2,3-dihydroxypropyl)-5-(4-pyridinyl)-2H-imidazo[4,5-b]pyridin-2-one.
E-16. 1,3-Dihydro-3-(2-dimethylaminoethyl)-5-(4-pyridinyl)-2H-imidazo[4,5-b]pyridin-2-one.
E-17. 1,3-Dihydro-3-(2-methoxyethyl)-5-(4-pyridinyl)-2H-imidazo[4,5-b]pyridin-2-one.
E-18. 1,3-Dihydro-3-[2-(4-morpholinyl)ethyl]-5-(4-pyridinyl)-2H-imidazo[4,5-b]pyridin-2-one.

F. 1,3-DIHYDRO-3-R-5-PY-2H-IMIDAZO[4,5-b]PYRIDINE-2-THIONES

F-1. 1,3-Dihydro-5-(4-pyridinyl)-2H-imidazo[4,5-b]pyridine-2-thione—To a warm (43° C.) solution containing 9.0 g. of 2,3-diamino-6-(4-pyridinyl)pyridine in 80 ml. of dimethylformamide was added with stirring 10.3 g. of 90% 1,1'-thiocarbonyldiimidazole, whereupon the temperature rose to 63° C. On allowing the reaction solution to cool to about 40° C., a solid began to separate. The mixture was chilled and the separated solid collected, washed with ether, triturated with cold ethanol-ether, washed again with ether and dried. The resulting solid was ground to a powder and boiled with ethanol to remove dimethylformamide. The solid was then collected and dried in vacuo at 100° C. to yield a 9.7 g. of 1,3-dihydro-5-(4-pyridinyl)-2H-imidazo[4,5-b]pyridine-2-thione, m.p. >330° C.

Following the procedure described in Example F-1 but using in place of 2,3-diamino-6-(4-pyridinyl)pyridine a molar equivalent quantity of the appropriate 2,3-diamino-6-PY-pyridine, it is contemplated that there can be obtained the 1,3-dihydro-5-PY-2H-imidazo[4,5-b]pyridine-2-thiones of Examples F-2 through F-8.

F-2. 1,3-Dihydro-5-(2-methyl-4-pyridinyl)-2H-imidazo[4,5-b]pyridine-2-thione.

F-3. 1,3-Dihydro-5-(3-methyl-4-pyridinyl)-2H-imidazo[4,5-b]pyridine-2-thione.

F-4. 1,3-Dihydro-5-(2-ethyl-4-pyridinyl)-2H-imidazo[4,5-b]pyridine-2-thione.

F-5. 1,3-Dihydro-5-(3-pyridinyl)-2H-imidazo-[4,5-b]pyridine-2-thione.

F-6. 1,3-Dihydro-5-(3-ethyl-4-pyridinyl)-2H-imidazo[4,5-b]pyridine-2-thione.

F-7. 1,3-Dihydro-5-(2,6-dimethyl-4-pyridinyl)-2H-imidazo[4,5-b]pyridine-2-thione.

F-8. 1,3-Dihydro-5-(3,5-dimethyl-4-pyridinyl)-2H-imidazo[4,5-b]pyridine-2-thione.

Following the procedure described in Example F-1 but using in place of 2,3-diamino-6-(4-pyridinyl)pyridine a molar equivalent quantity of the appropriate 3-amino-2-RNH-6-(4-pyridinyl)pyridine, it is contemplated that there can be obtained the corresponding 1,3-dihydro-3-R-5-(4-pyridinyl)-2H-imidazo[4,5-b]pyridine-2-thiones of Examples F-9 through F-18.

F-9. 1,3-Dihydro-3-methyl-5-(4-pyridinyl)-2H-imidazo[4,5-b]pyridine-2-thione.

F-10. 3-Ethyl-1,3-dihydro-5-(4-pyridinyl)-2H-imidazo[4,5-b]pyridine-2-thione.

F-11. 1,3-Dihydro-3-isopropyl-5-(4-pyridinyl)-2H-imidazo[4,5-b]pyridine-2-thione.

F-12. 3-n-Butyl-1,3-dihydro-5-(4-pyridinyl)-2H-imidazo[4,5-b]pyridine-2-thione.

F-13. 3-n-Hexyl-1,3-dihydro-5-(4-pyridinyl)-2H-imidazo[4,5-b]pyridine-2-thione.

F-14. 1,3-Dihydro-3-(2-hydroxyethyl)-5-(4-pyridinyl)-2H-imidazo[4,5-b]pyridine-2-thione.

F-15. 1,3-Dihydro-3-(2,3-dihydroxypropyl)-5-(4-pyridinyl)-2H-imidazo[4,5-b]pyridine-2-thione.

F-16. 1,3-Dihydro-3-(2-dimethylaminoethyl)-5-(4-pyridinyl)-2H-imidazo[4,5-b]pyridine-2-thione.

F-17. 1,3-Dihydro-3-(2-methoxyethyl)-5-(4-pyridinyl)-2H-imidazo[4,5-b]pyridine-2-thione.

F-18. 1,3-Dihydro-3-[2-(4-morpholinyl)ethyl]-5-(4-pyridinyl)-2H-imidazo[4,5-b]pyridine-2-thione.

The usefulness of the compounds of formula I or salt thereof as a cardiotonic agent is demonstrated by its effectiveness in standard pharmocological test procedures, for example, in causing a significant increase in contractile force of the isolated cat atria and papillary muscle. A detailed description of this test procedure appears in U.S. Pat. No. 4,072,746, issued Feb. 7, 1980.

When tested by said isolated cat atria and papillary muscle procedure, the compounds of formula I or salts thereof when tested at doses of 10 and 30 μg./ml., were found to cause significant increase, that is, greater than 25% in papillary muscle force and a significant increase, that is, greater than 25%, in right atrial force, while causing a lower percentage increase (about one-third or less than the percentage increase in right atrial force or papillary muscle force) in right atrial rate. For example, when tested at 10 and 30 μg./ml. by this procedure, 1,3-dihydro-5-(4-pyridinyl)-2H-imidazo[4,5-b]-pyridin-2-one was found to cause respective percentages increases in papillary muscle force, right atrial force and right atrial rate of: 45%, 65% and 14%; and 66%, 153% and 26%, respectively. Similarly, when tested at 3, 10 and 30 μg./ml. by this procedure, 1,3-dihydro-5-(4-pyridinyl)-2H-imidazo-[4,5-b]pyridine-2-thione was found to cause respective increases in papillary muscle force, right atrial force and right atrial rate of: 27%, 16% and 0%; 66%, 40% and 16%; and 174%, 73% and 29%.

The present invention includes within its scope a cardiotonic composition for increasing cardiac contractility, said composition comprising a pharmaceutically-acceptable carrier and, as the active component thereof, the cardiotonic compound of formula I or pharmaceutically-acceptable acid-addition salt thereof. The invention also includes within its scope the method for increasing cardiac contractility in a patient requiring such treatment which comprises administering to such patient an effective amount of cardiotonic compound of formula I or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

They can be sterilized, for example by filtration through a bacteria-retaining filter, by incorporation of sterilizing agents in the compositions, by irradiation or by heating. They can also be manufactured in the form of sterile solid compositions which can be dissolved in sterile water or some other sterile injectable medium immediately before use.

The percentages of active component in said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utlizing the best judgement on the patient's behalf.

We claim:

1. A 1,3-dihydro-3-R-5-PY-2H-imidazo[4,5-b]pyridin-2-one or -2-thione having the formula

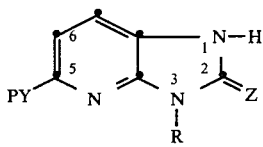

where Z is O, or S, R is hydrogen, lower-alkyl, lower-hydroxyalkyl, 2,3-dihydroxypropyl, lower-alkoxyalkyl or Y-NB where Y is lower-alkylene having at least two carbon atoms between its connecting linkages and NB is di-(lower-alkyl)amino or 4-morpholinyl, and PY is 4- or 3-pyridinyl or 4- or 3-pyridinyl having one or two lower-alkyl substituents, or pharmaceutically-acceptable acid-addition salt thereof.

2. A compound according to claim 1 where PY is 4-pyridinyl or 3-pyridinyl.

3. A compound according to claim 1 where Z is S.

4. A compound according to claim 1 where Z is O.

5. A compound according to claim 1 where R is hydrogen, methyl, ethyl or 2-hydroxyethyl.

6. A compound according to claim 1 where R is hydrogen, PY is 4-pyridinyl and Z is S.

7. A compound according to claim 1 where R is hydrogen, PY is 4-pyridinyl and Z is O.

8. A cardiotonic composition for increasing cardiac contractility, said composition comprising a pharmaceutically-acceptable inert carrier and, as the active component thereof, an effective amount of a cardiotonic 1,3-dihydro-3-R-5-PY-2H-imidazo[4,5-b]pyridin-2-one or -2-thione or pharmaceutically-acceptable acid-addition salt thereof, where Z is O or S, R is hydrogen, lower-alkyl, lower-hydroxyalkyl, 2,3-dihydroxypropyl, lower-alkoxyalkyl or Y-NB where Y is lower-alkylene having at least two carbon atoms between its connecting linkages and NB is di-(lower-alkyl)amino or 4-morpholinyl, and PY is 4- or 3-pyridinyl or 4- or 3-pyridinyl having one or two lower-alkyl substituents.

9. A composition according to claim 8 where the active component is 1,3-dihydro-5-(4-pyridinyl)-2H-imidazo[4,5-b]-pyridin-2-one or pharmaceutically-acceptable acid-addition salt thereof.

10. A composition according to claim 8 where the active component is 1,3-dihydro-5-(4-pyridinyl)-2H-imidazo[4,5-b]-pyridine-2-thione or pharmaceutically-acceptable acid-addition salt thereof.

11. The method for increasing cardiac contractility in a patient requiring such treatment which comprises administering orally or parenterally in a solid or liquid dosage form to such patient an effective amount of the cardiotonic 1,3-dihydro-3-R-5-PY-2H-imidazo[4,5-b]pyridin-2-one or -2-thione or pharmaceutically-acceptable acid-addition salt thereof, where Z is O or S, R is hydrogen, lower-alkyl, lower-hydroxyalkyl, 2,3-dihydroxypropyl, lower-alkoxyalkyl or Y-NB where Y is lower-alkylene having at least two carbon atoms between its connecting linkages and NB is di-(lower-alkyl)amino or 4-morpholinyl, and PY is 4- or 3-pyridinyl or 4- or 3-pyridinyl having one or two lower-alkyl substituents.

12. A 3-amino-2-RNH-6-PY-pyridine or pharmaceutically-acceptable acid-addition salt thereof, where R is hydrogen, lower-alkyl, lower-hydroxyalkyl, 2,3-dihydroxypropyl, lower-alkoxyalkyl or Y-NB where Y is lower-alkylene having at least two carbon atoms between its connecting linkages and NB is di-(lower-alkyl)amino or 4-morpholinyl, and PY is 4- or 3-pyridinyl or 4- or 3-pyridinyl having one or two lower-alkyl substituents.

13. A compound according to claim 12 where R is hydrogen methyl, ethyl or 2-hydroxyethyl.

14. A compound according to claim 12 where PY is 4-pyridinyl or 3-pyridinyl.

* * * * *

UNITED STATES PATENT AND TRADEMARK OFFICE
CERTIFICATE OF CORRECTION

PATENT NO. : 4,294,836

DATED : October 13, 1981

INVENTOR(S) : George Y. Lesher and Ruth F. Brundage

It is certified that error appears in the above-identified patent and that said Letters Patent are hereby corrected as shown below:

Column 1, line 63, "3-pyridinyl" should read -- 2-pyridinyl --.

Column 13, claim 1, line 19, delete the comma between "O" and "or".

Signed and Sealed this

Eighth Day of June 1982

|SEAL|

Attest:

GERALD J. MOSSINGHOFF

Attesting Officer     Commissioner of Patents and Trademarks